US005667471A

United States Patent [19]
Weller et al.

[11] Patent Number: 5,667,471
[45] Date of Patent: Sep. 16, 1997

[54] PROSTHETIC DEVICE WITH A RETAINING STRAP

[75] Inventors: James M. Weller, Blaine; John C. Field, St. Paul, both of Minn.

[73] Assignee: Gain, Incorporated, St. Paul, Minn.

[21] Appl. No.: 638,730

[22] Filed: Apr. 29, 1996

[51] Int. Cl.$^6$ ........................................................ A61F 5/00
[52] U.S. Cl. ..................................................................... 600/39
[58] Field of Search ................................. 600/38, 39, 40, 600/41; 604/349, 350, 351, 332, 353

[56] References Cited

U.S. PATENT DOCUMENTS

| | | |
|---|---|---|
| 1,206,324 | 4/1916 | Hart . |
| 1,362,398 | 12/1920 | Crawford et al. . |
| 1,383,944 | 7/1921 | Hart . |
| 1,585,861 | 5/1926 | Huff . |
| 2,471,360 | 2/1947 | Thome . |
| 2,868,192 | 1/1959 | Dannen . |
| 2,899,957 | 8/1959 | Briggs . |
| 3,495,588 | 2/1970 | Walters . |
| 3,648,700 | 3/1972 | Warner . |
| 3,920,007 | 11/1975 | Line . |
| 3,939,827 | 2/1976 | Brunsletter . |
| 3,982,530 | 9/1976 | Storch . |
| 4,074,712 | 2/1978 | Wright . |
| 4,194,502 | 3/1980 | Eckels . |
| 4,224,933 | 9/1980 | Reiling . |
| 4,449,521 | 5/1984 | Panzer . |
| 4,615,337 | 10/1986 | Allinson . |
| 4,672,954 | 6/1987 | Panzer . |
| 4,893,616 | 1/1990 | Immonen . |
| 4,972,849 | 11/1990 | Park . |
| 5,360,390 | 11/1994 | Maanum . |

FOREIGN PATENT DOCUMENTS

| | | |
|---|---|---|
| 2221116 | 10/1974 | France . |
| 2355495 | 6/1975 | France . |

OTHER PUBLICATIONS

Exhibit A Letter from Fre-San Products Mfg. Co. dated Feb. 23, 1970, and attached product brochure (8 pages).
Exhibit B Advertisement for Spencer Products (1 page).
Exhibit C Sex Aids & Novelties pp. 1,6 (2 pages).
Exhibit D Aphrodisia catalog cover and 2 unnumbered pages (3 pages).
Exhibit E Advertisement for Bier's Erectruss (2 pages).
Exhibit F Spectra catalog cover and 3 unnumbered pages (4 pages).
Exhibit G Snap Products catalog, 3 unnumbered pages (3 pages).
Exhibit H Original Sales, Inc. catalog (1972), 2 unnumbered pages (2 pages).
Exhibit I Therapeutic Products Co. catalog, 4 unnumbered pages (4 pages).
Exhibit J Twentieth Century Surgical Supplies, Inc. catalog, 4 unnumbered pages (4 pages).
Exhibit K Medco Sales Advertisement (1 page).
Exhibit L Adult World catalog cover, pp. 16, 17 (1973) (3 pages).
Exhibit M Select Items catalog cover, pp. 2–4, 6, 7 (1974) (4 pages).
Exhibit N PAP, Co. catalog, 2 unnumbered pages (2 pages).
Exhibit O Safe-P-Products catalog envelope dated Nov. 16, 1967, cover and 3 unnumbered pages (4 pages).
Exhibit P Leisure Time Products Advertisement dated May, 1975 (2 pages).
1994 Adam & Eve catalog pp. 1, 44 (copyright pages), 48 & 62.
Apr. 1991 Mail Potency Clinic's response to product inquiry letter.
Nov. 1990 Minneapolis Star Tribune article.
1985 FDA filing K850966 (best available copy).
1984 FDA filing K840259 (best available copy).

*Primary Examiner*—Debra S. Brittingham
*Attorney, Agent, or Firm*—Merchant, Gould, Smith Edell, Welter & Schmidt, P.A.

[57] ABSTRACT

A device is provided for use as a prosthesis in supporting the penis of a wearer, during intercourse. The prosthesis comprises an elongate trough member and an arrangement for maintaining the trough member in operative association over the user's penis, during performance of intercourse. A retaining strap is provided to facilitate retaining of the prosthesis in place.

20 Claims, 9 Drawing Sheets

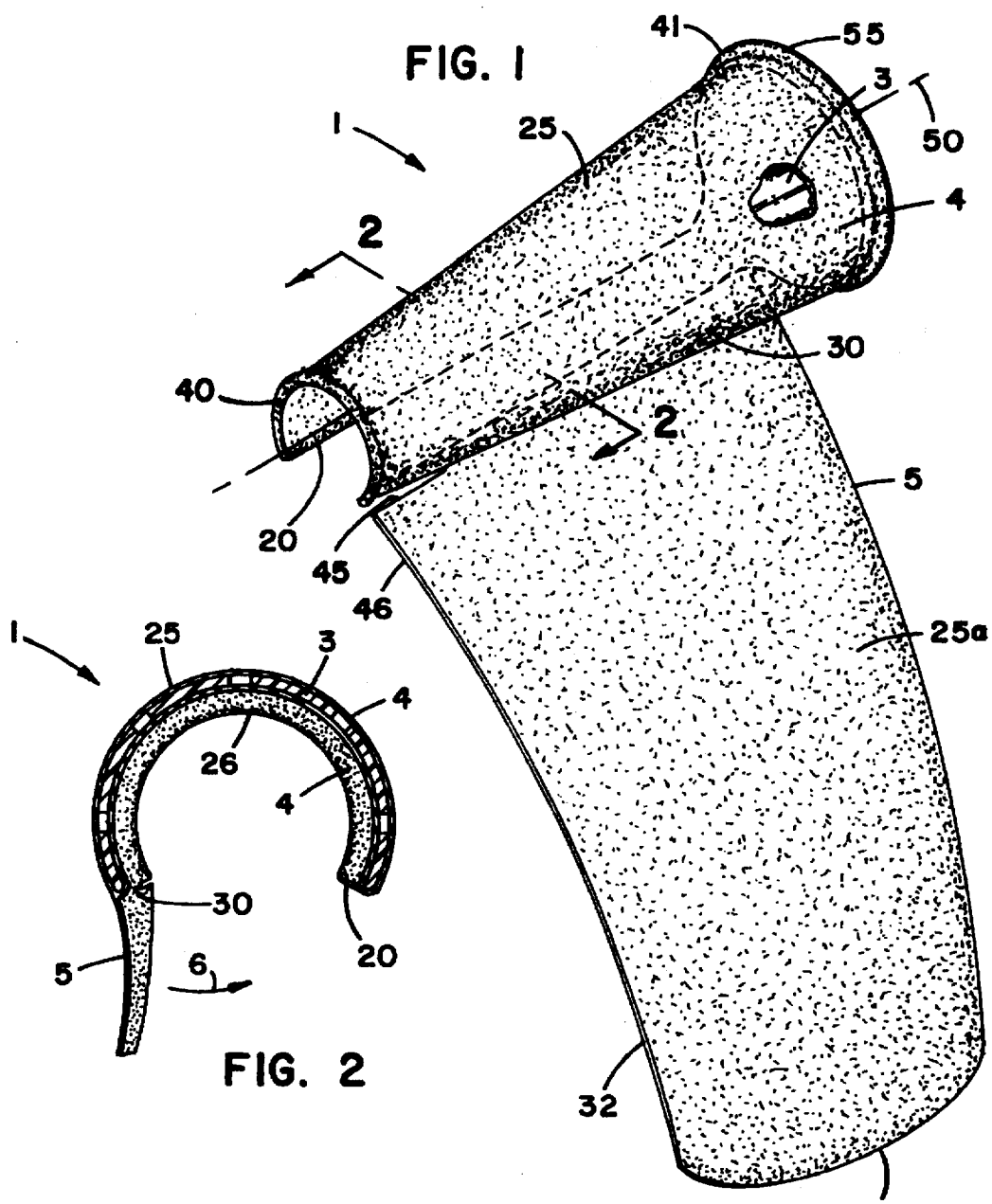

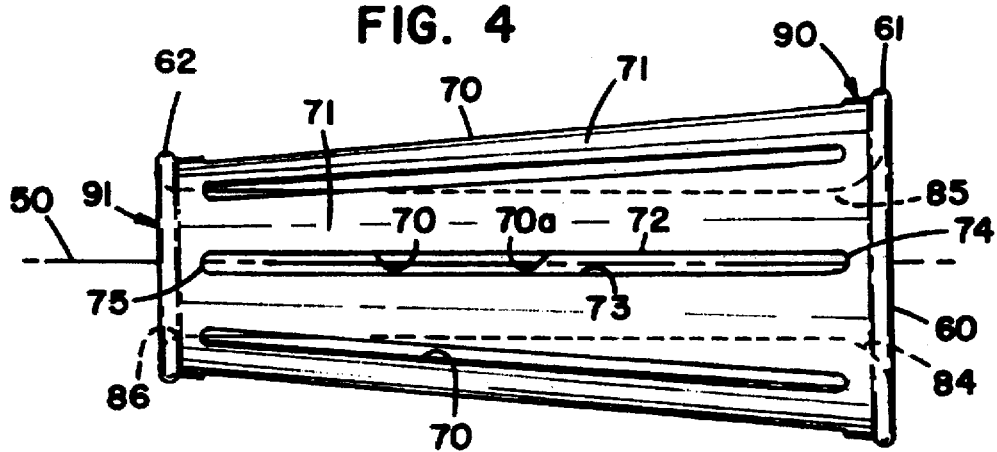
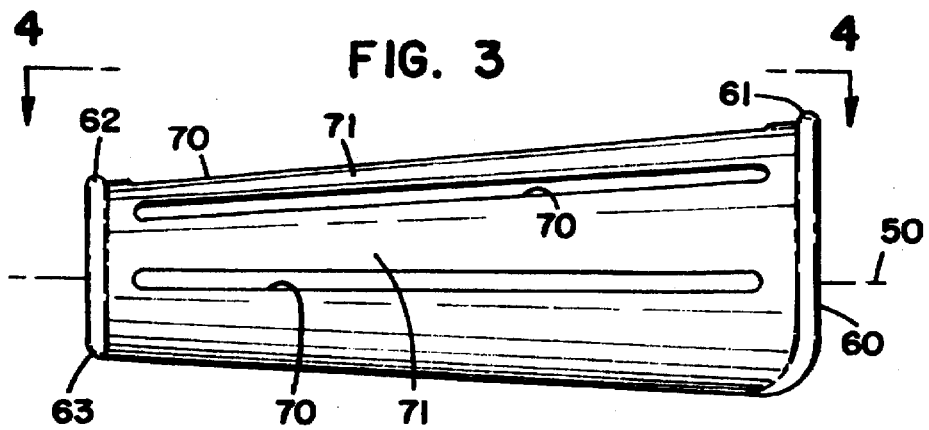
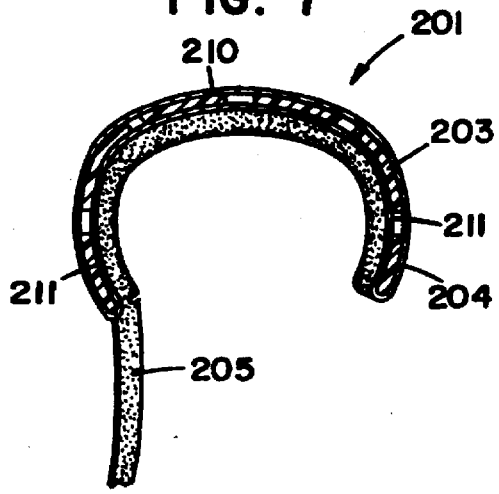
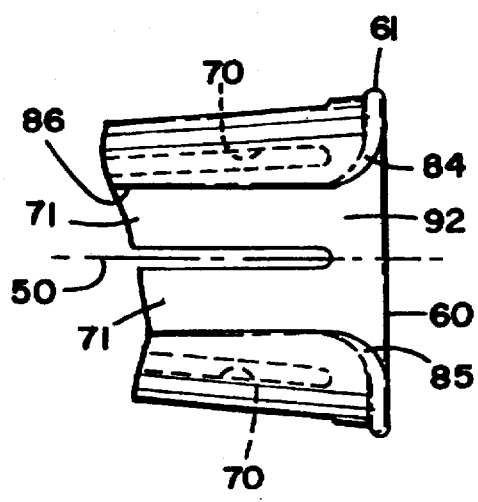

5,667,471

1

PROSTHETIC DEVICE WITH A RETAINING STRAP

FIELD OF THE INVENTION

The present invention generally relates to prosthetics and prosthetic devices. More specifically, the invention concerns devices utilizable to support the human penis, during sexual activity.

GENERAL BACKGROUND OF THE INVENTION

For a variety of reasons, many human males are totally or partially sexually dysfunctional. Causes or factors relating to this dysfunctionality have been widely studied and are under continual examination. In general, a variety of causes and/or factors are known, including both physical (medical) and mental (psychological) ones.

In many instances the dysfunction is only partial. For example, the male may be physically capable of engorging and thus enlarging the penis, but cannot obtain a sufficiently rigid erection for sexual activity, or cannot maintain one for a sufficient period of time to satisfactorily complete intercourse.

A wide variety of devices have been developed to assist the sexually dysfunctional male in maintaining an erection. Some are surgical implants, which when manipulated simulate a rigid erection. Others are external aids which, when applied or mounted, serve to partially simulate an erect penis. It is the latter type (i.e., external) which is of particular interest herein.

SUMMARY OF THE INVENTION

According to one aspect to the present invention there is provided a prosthesis for use by a human male in supporting the penis during sexual intercourse. The preferred prosthesis comprises an elongate trough member of unitary, molded, construction, without any seams, sized to fit over the penis of a user at a location immediately in front of the pubic bone, with the trough member having a longitudinal slot extending completely therethrough, and the trough member having first and second rounded ends. The longitudinal slot is positioned under the penis, in preferred use. The prosthesis has a retaining construction secured to the trough member second end for maintaining the trough member in operative association over the user's penis, during the performance of sexual intercourse, with the retaining construction preferably comprising a retaining tab, and a retaining strap having structure thereon for selective locking engagement with the retaining tab. Preferably both the retaining tab and retaining strap are thinner than the second end of the trough member. Also, preferably both the retaining strap and the retaining tab are secured to the trough member second end so that an outer shoulder is formed along the trough member second end, between each of the retaining strap and retaining tab, and an outer surface of the trough member.

In a preferred embodiment the retaining tab has a first end whereat it is molded to the trough member; and, (1) a first end of the retaining tab has a first dimension of width; and, (2) the tab is configured to have a second dimension of width, at a portion thereof spaced from said trough member, which is greater than the first dimension. In certain preferred embodiments, the second dimension of the tab is at least 0.75 times larger than the first dimension. Typically, the tab second dimension will be 1 to 4 times larger than the first dimension. In some preferred applications, the first dimension of width will be within the range of about 0.25 to 0.5 inches and the second dimension of width will be in the range of about 0.5 to 1.0 inches.

In a typical embodiment, the prosthesis has a trough member with an overall length in projection of 2 to 4 inches. In typical applications, the trough member first end also has an inside edge having a radius of curvature that is less than 0.03 inches; and, the trough member first end has an outside edge having a radius of curvature between 0.02–0.03 inches. Also, typically the trough member second end has an inside edge having a radius of curvature that is less than 0.03 inches; and, the trough member second end has an outside edge having a radius of curvature between 0.05–0.1 inches.

In typical applications, the prosthesis has a trough member first end with a thickness of about 0.02–0.08 inches; and, a trough member second end with a thickness of about 0.2–0.3 inches. In certain preferred embodiments, the prosthesis has a trough member first end molded to a radius of curvature of about 0.55–0.58 inches; and, a trough member second end molded to a radius of curvature of about 0.6–0.75 inches. For some preferred embodiments, the trough member is a molded construction comprising flexible urethane or latex. For some preferred embodiments the thickness of the trough member decreases laterally from the center to the edges or corners.

The drawings constitute a portion of the specification and include exemplary embodiments of the present invention. It will be understood that in some instances relative component sizes and material thicknesses may be shown exaggerated, to facilitate an understanding of the invention.

BRIEF DESCRIPTION OF THE DRAWINGS

FIG. 1 is a perspective view of a prior art prior art device shown in U.S. Pat. No. 5,360,390.

FIG. 2 is a fragmentary cross-sectional view of the prior art device shown in FIG. 1, taken generally along line 2—2 thereof.

FIG. 3 is a side elevation view of a prior art component of the prior art device illustrated in FIG. 1.

FIG. 4 is a top plan view of the prior art component depicted in FIG. 3, taken generally from the point of view of line 4—4 thereof.

FIG. 5 is a fragmentary, bottom plan view of the prior art arrangement shown in FIG. 3.

FIG. 6 is a view of the prior art arrangement shown in FIG. 1, depicted operably mounted for use.

FIG. 7 is a view analogous to FIG. 2, for an alternate prior art device also depicted in U.S. Pat. No. 5,360,390.

FIG. 10 also depicting an arrangement shown in U.S. Pat. No. 5,360,390.

FIG. 11 also depicting an arrangement shown in U.S. Pat. No. 5,360,390.

FIG. 15 also showing prior art arrangement depicted in U.S. Pat. No. 5,360,390.

FIG. 17 being from the view point of line 17—17, FIG. 16.

FIG. 21 depicting, in phantom, an optional condom or lubricated cover which may be utilized in association with the arrangement.

DETAILED DESCRIPTION

Figure 8:
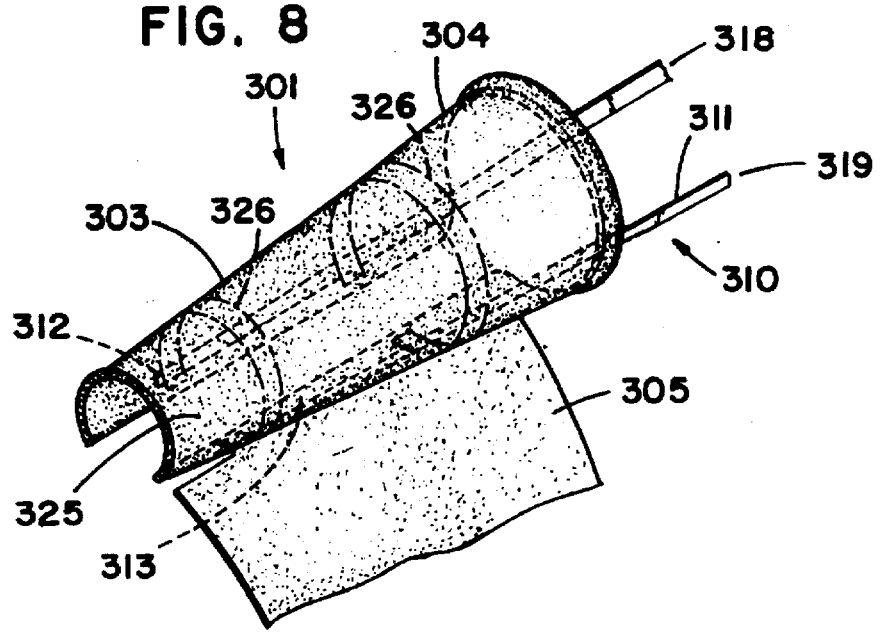
FIG. 8 is a fragmentary perspective view of a second alternate prior art device also depicted in U.S. Pat. No. 5,360,390; the perspective of FIG. 8 being generally analogous to that of FIG. 1.

Herein a detailed description of the present invention is provided. The description is made with reference to accompanying drawings, and specific features of the preferred embodiment depicted therein. It is to be understood that the specific features of the drawings are intended to be exemplary, for a general understanding of the basic principles of the present invention.

The present invention is an improvement in the arrangements described in U.S. Pat. No. 5,360,390 issued Nov. 1, 1994, and presently owned by Gain, Inc. of Minneapolis, Minn., the assignee of the present invention. Before specific improvements relating to the present invention are described, a specific description of the prior art arrangements of U.S. Pat. No. 5,360,390 will be presented. The complete disclosure of U.S. Pat. No. 5,360,390 is incorporated herein by reference.

I. The Arrangements of U.S. Pat. No. 5,360,390

A. FIGS. 1–6

Reference numeral 1, FIG. 1, generally refers to a device or arrangement according to a first device described in U.S. Pat. No. 5,360,390. The device 1 comprises an elongate, generally cylindrical trough member 3 enclosed within a sheath 4. The sheath 4 includes attached thereto, or preferably formed integrally and continuously therewith, an elongate mounting flap or tail 5. As will be apparent from the following, the sheath 4 and tail 5 together comprise retaining means for maintaining the trough member 3 in operative association with a user's penis, during use; i.e. during performance of sexual intercourse.

Before specific details of the construction of device 1 are presented, a brief description of its utilization and operation will be presented. With respect to this, attention is directed to FIGS. 1, 2 and 6. As will be understood by reference to FIG. 2, tail 5 is generally an elongate thin, flexible member.

In use, device 1 of U.S. Pat. No. 5,360,390 was to be fitted over a partially engorged, i.e. typically a partially enlarged and elongated but insufficiently rigid for satisfactory sexual activity, penis 10. The device 1 is generally and preferably sized to snugly fit in extension between a region 12 of the pubic bone, to a point behind the glans 13. The device 1 was secured in position by wrapping tail 5 around the penis 10, and the trough member 3 in combination, as shown in FIG. 6. In general, the wrapping would preferably have been in the direction indicated by arrow 6, FIG. 2.

It was preferred in U.S. Pat. No. 5,360,390 that in use a condom 15 be positioned over the mounted device 1. That is, a condom 15 was utilized as a sleeve to maintain comfortable, secure, mounting of the device 1. In some instances a condom allowing for a larger than average diameter male may have been preferred for comfort. If it was desired that the condom 15 not interfere with procreation, the end 16 thereof can be punctured or otherwise cut open to allow passage of semen therethrough.

An important feature in U.S. Pat. No. 5,360,390 regarding utilization of the device 1 can be readily understood by reference to FIG. 6. In general, device 1 was preferably mounted over the partially engorged penis 10, rather than under same. That is, trough member 3, preferably generally cylindrical in configuration, included an open slot 20, FIG. 1, therein, i.e. trough member 3 had an open C-shaped configuration in cross-section. In preferred use in U.S. Pat. No. 5,360,390, the device 1 was fitted over the penis, with slot 20, i.e. the open part of the C-shaped cross-section, directed generally downwardly or away from the belly. Reasons for this will be apparent from further descriptions herein below.

To facilitate mounting in this manner, in U.S. Pat. No. 5,360,390 it was described that preferably the "open" portion of the C-shaped cross-section comprise a gap of at least about 0.5 inches across, for the average male, FIG. 6, and that it was foreseen that a gap of about 0.75 to about 1.5 inches would be preferred. The "gap" in that instance was the distance between opposite edges of the trough member 3, across the open part of the "C". It was also described that if a circular radius was used for the C-shaped cross-section, typically a gap extending across an arc of 50° to 110° would be preferred, again for the average male.

Specific features regarding the construction of device 1, provided for comfortable and convenient use, both for the user, and for the user's sex partner. In U.S. Pat. No. 5,360,390 it was described that details of preferred construction with respect to each of the trough member 3, sheath 4 and tail 5, were of significance with respect to this.

Referring to FIG. 1, in U.S. Pat. No. 5,360,390 it was described that preferably the sheath 4, in which the trough member 3 was enclosed, was provided of a relatively soft, smooth, material which exhibited a relatively high coefficient of friction against human skin. In was also described that in preferred embodiments, the inner surface of the sheath was pebbled, to facilitate retention in place during use. Therein, the term "relatively high coefficient of friction" in that context was meant to refer to a coefficient sufficiently high so that the device 1, when mounted, was not likely to slide relative to the user's penis, during normal intercourse activity. Thus, at least in part as a result of that relatively high coefficient of friction, device 1 would remain in place, during intercourse. In U.S. Pat. No. 5,360,390 it was described that a variety of suitable materials may be utilized with the sheath 4, including latex rubber materials or the like; and, that one such material was the material from which external urinary catheters are formed. It was also stated that it would be readily understood from the previous description of use, that a relatively high degree of friction between an outer surface 25 of sheath 4, or outer surface 25a of tail member 5, and the user's sex partner was of little concern, since in preferred use the device 1 would be received beneath a condom 15 or the like, which could provide for comfortable lubricated movement and natural feel. Referring to FIG. 2, the relatively high coefficient of friction to prevent sliding in the area of inner surface 26, however, would again help secure device 1 in place on a wearer, even during relatively rigorous sexual activity.

In U.S. Pat. No. 5,360,390 it was stated that the overall thickness of sheath 4 could be varied, as long as it provided for sufficient protection of core 3, and comfort for the user and the user's partner. Further, it was foreseen that if polypropylene or polyethylene was utilized as the trough material underneath a latex sheath material, in general an overall thickness of about 0.1 to 0.3 inches, i.e. thickness from either one of surfaces 25 or 26 through to the trough member 3, FIG. 2 would in general be useable and preferred.

Referring to FIG. 1, tail 5 was shown mounted along sheath 4 at region 30, along substantially an entire longitudinal extension of device 1. In U.S. Pat. No. 5,360,390 it was described that tail 5 may comprise a separate and different material from sheath 4, merely attached to sheath 4 in region 30. In the alternative, and as shown in the preferred embodiment of FIG. 1, it was described that tail piece 5 may preferably comprise a thin, flexible extension of the same material as sheath 4, molded, extruded or otherwise generated continuously with sheath 4 and region 30, i.e. without a seam (seamless). Thus, for the arrangement shown in FIG. 1 of U.S. Pat. No. 5,360,390, it was described that tail 5 preferably comprised a flexible extension of the same latex from which sheath 4 was preferably formed.

Referring to FIG. 1, the tail 5 depicted therein was shown in a preferred configuration of U.S. Pat. No. 5,360,390 having an outer periphery 32 with the generally U shaped configuration, i.e. wide in region 30 and, narrowing to a rounded point at region 35. Thus, when wrapped around sheath 4 and a wearer's penis, FIG. 6, tail 5 would tend to build up in thickness, to a maximum extent, in central portion 37 of the sheath 4. This would prevent a substantial bulge in the material near either of ends 40 and 41 of the sheath. Avoidance of bulges in these regions may be desirable, for both comfort of the wearer and also comfort of the wearer's partner. In general, in U.S. Pat. No. 5,360,390, it was described that tail 5 should be long enough to wrap around the arrangement at least about 1.5–2 times. In typical application a length of about 5 to 11 inches would be sufficient.

Referring to end 40, as described in U.S. Pat. No. 5,360, 390 for the preferred embodiment, sheath 5, in region 30, included a notch or slot 45 thereat creating mounting flap 46. This facilitated comfort of the wearer should the wearer have substantial foreskin immediately behind the glans. Such foreskin, if present, could be pulled backwardly over sheath 4 and then be wrapped underneath tail 5; notch 45 and flap 46 accommodating, comfortably, the presence of the foreskin. In the absence of notch 45 and flap 46 such foreskin would tend to be pinched in this location, causing discomfort and possible injury, especially during intercourse. In U.S. Pat. No. 5,360,390 it was stated that a notch or slot 45 of about 0.5 to 1.5 inches in length (and preferably about 1 inch) would typically be sufficient for achievement of the desired effect.

In U.S. Pat. No. 5,360,390 it was stated that many of the advantageous features of device 1 result from the nature and construction of trough member 3. In general, for the preferred embodiment illustrated in FIGS. 1 and 2, it was stated that trough member 3 is formed from a relatively thick, smooth material and that a variety of materials may be utilized. It was stated that preferred materials include polyethylene and polypropylene plastics, or similar polymeric plastics.

It was also stated in U.S. Pat. No. 5,360,390 that preferably the material from which trough member 3 was formed was sufficiently radially-rigid so that it did not tend to compress over the user's penis, causing discomfort or impairing circulation, as tail 5 was wrapped tightly therearound and/or during intercourse. That is, it was stated that preferably core 3 be constructed in a manner such that it would tend to resist harmful "radial" collapse, i.e. an uncomfortable tightening or pinching down toward central longitudinal axis 50 thereof, under the type of pressures that would be associated either with the wrapping of tail 5, or intercourse itself. In U.S. Pat. No. 5,360,390 it was stated that one manner in which that could be controlled was through utilization of an appropriately strong plastic, of appropriate thickness. The device shown in FIG. 1 of U.S. Pat. No. 5,360,390 included an end rib or bead 55 which facilitated resistance to radial collapse. Therein that resistance to radial collapse would be generally referred to as "substantial radial-rigidity". That term and variants thereof in U.S. Pat. No. 5,360,390, were meant to refer to a trough member 3 sufficiently rigid or resistant to radial collapse, so as not to uncomfortably tighten over a user's penis, during intercourse. Bead 55 in U.S. Pat. No. 5,360,390 also facilitated comfort, as it broadened an end of the device whereat it was positioned against a user's pubic area.

Trough member 3 was depicted in U.S. Pat. No. 5,360, 390, without sheath 4 and tail 5 thereon, in FIGS. 3, 4 and 5. Referring to FIG. 3, trough member 3 included an end 60, which generally corresponded to end 41, FIG. 1. End 60 was shown with the molded outer bead 61 thereon, which in cooperation with sheath 4 formed rib 55. In U.S. Pat. No. 5,360,390, for the preferred embodiments shown, rib or bead 61 represented a relatively thick, strong, structural component which would facilitate resistance to radial collapse, of trough member 3. That, as explained above, was considered advantageous for the arrangement. Also for the arrangement shown in FIG. 3, in U.S. Pat. No. 5,360,390 a second bead 62 positioned at an end 63 opposite to end 60 was used to further facilitate radial strength. The second bead 62 was described as preferably of about the same thickness as the first bead 61.

In general, in U.S. Pat. No. 5,360,390 it was described that it would be desirable that trough member 3 be constructed in a manner allowing for a specific type of longitudinal flexibility, i.e. a type of flexibility along its length of extension. That would facilitate comfort for the wearer, as the extent of penis engorgement fluctuates during sex activity. Further, it would facilitate both the wear's comfort and the wearer's partner's comfort, during the sex act. One problem described in U.S. Pat. No. 5,360,390 with many other types of arrangements was that they were so rigid in extension, they were very uncomfortable for the wear's partner during normal intercourse, or in various sex positions. In both U.S. Pat. No. 5,360,390 and the present application, the term "substantial longitudinal flexibility" and variants thereof refer to that flexibility; i.e. flexibility sufficient for comfort and to allow for fluctuation in penile engorgement while at the same time sufficiently rigid to simulate erection in use. A specific type of flexibility referred to in that context, was one which resulted from features detailed below.

For the arrangement depicted in FIGS. 1 and 3, in U.S. Pat. No. 5,360,390 it was described that substantial longitudinal flexibility was provided at least in part by means of spaced slots 70. Between slots 70, strip 71 would provide for a type of longitudinal flexibility, facilitating comfort. In U.S. Pat. No. 5,360,390 it was described that preferably slots 70 be provided sufficiently wide such that no site of pinching between opposite edges, for example opposite edges 72 and 73 of slot 70a, was likely. Also, it was described that preferably ends 74, 75 of the slots 70 be rounded, to inhibit splitting and to facilitate comfort.

For the preferred embodiment illustrated in FIG. 1, in U.S. Pat. No. 5,360,390 it was described that preferably the slots were each at least about 1/32 to 1/8 inches wide. Also, it was described that preferably each slot extend for at least about 60%, and more preferably at least about 85%, of the overall length of trough member 3, to facilitate the selected type longitudinal flexibility along most of the longitudinal extension of device 1. In general, it was described that a preferred spacing between adjacent slots was about .05 to 1.5 inches, although a variety of spacings could be utilized. Referring to FIGS. 3 and 4 of U.S. Pat. No. 5,360,390, slots 70 were shown diverging, in extension from ends 75 to end 74, relative to one another. That arrangement resulted in part through accommodation of tapering described below for the overall longitudinal extension of member 3. In U.S. Pat. No. 5,360,390 it was described that in some applications slots 70 may be prepared extending generally parallel to one another, rather than in the diverging pattern illustrated.

For arrangements such as those depicted, in U.S. Pat. No. 5,360,390 it was stated that preferably the material from which the trough member was formed had a thickness of about 1/16 to 1/8 inches, with each radial bead providing for a total thickness of about 1/8 to 3/8 inches thereat. That is, it was stated that preferably each radial bead was about 1/16 to 1/4 inch thick.

In U.S. Pat. No. 5,360,390 it was stated that advantages due to a type of increased flexibility indeed resulted from a slotted arrangement. In particular, it was stated that strips 71 were independently somewhat flexible, and allowed some movement for comfort. According to U.S. Pat. No. 5,360,390 the slots 70 could be provided in member 3 in a variety of manners including by being cut or stamped therein, or by being molded therein during a molding operation.

According to U.S. Pat. No. 5,360,390 in preferred applications member 3, and thus device 1 when sheath 4 is provided over member 3, was not perfectly cylindrical, but rather had an advantageous configuration including a first inside or inner radius of curvature at end 60 and a second radius at end 63, the radius at end 60 being larger than the radius at end 63. Also, according to U.S. Pat. No. 5,360,390 preferably at end 60 corners 84 and 85 in slot 86 (corresponding to slot 26 when covered by sheath 4, FIG. 1) were flared somewhat, for comfort. Thus, member 3, and resulting device 1, included a relatively large radius flared end 90, sized for comfortable placement against the pubic bone of the wearer. Opposite end 91, however, according to U.S. Pat. No. 5,360,390 preferably had a relatively small radius of curvature in comparison, facilitating secure placement behind the glans of the wearer, FIG. 5. Therein, the term "radius" in that context was meant to refer to the radius of curvature of the inner surface 92 of device 1 or the inner surface 26 of member 3, FIG. 5.

It is noted that the embodiment of FIGS. 1-5, as described in U.S. Pat. No. 5,360,390, was provided with member 3 having a generally circular C-shaped configuration. According to U.S. Pat. No. 5,360,390 alternate embodiments were available, for example wherein a C-shaped curve was provided with a more flattened and oval configuration. Such an embodiment was illustrated in FIG. 7, as discussed below. In U.S. Pat. No. 5,360,390 it was stated that for such arrangements dimensions generally similar to those described above would be preferred, except for the slightly flattened configuration to facilitate comfort for some wearers.

According to U.S. Pat. No. 5,360,390 in typical applications, for most males, the internal radius of end 90 would preferably be about 0.5 to 1.0 inches larger than the internal radius of end 91. Of course, there is a wide variety of differences in the circumference of the penis, among human males. According to U.S. Pat. No. 5,360,390, depending upon the wearer, the overall internal radius of curvature of end 91 would generally preferably be about 0.5 to about 1.5 inches.

Referring to FIG. 1, according to U.S. Pat. No. 5,360,390 in the embodiment illustrated a relatively constant increase in the internal radius was shown, along extension from end 40 to end 41. That is, the arrangement illustrated in FIG. 1 represented, substantially, a truncated conical shape. That resulted, FIG. 3, from relatively constant increase in radius from end 91 to end 90 of member 3, with a relatively constant thickness of sheath 4, FIG. 1.

According to U.S. Pat. No. 5,360,390, advantages could be obtained, in the absence of a constant increase in radii of curvature. That is, according to U.S. Pat. No. 5,360,390 for some embodiments a relatively constant radius of curvature could be utilized over a portion of the device, with an end flare or widening in the end corresponding to end 41, FIG. 1. The particular choice would depend, in part, upon the amount of flaring over the longitudinal extension device 1, considered to be most comfortable for any particular wearer.

According to U.S. Pat. No. 5,360,390 a variety of dimensions could be utilized for devices 1, due to variations in the human population. In general, according to U.S. Pat. No. 5,360,390 the device 1 should be constructed to be of appropriate length to snugly fit between the pubic bone and the glans of the wearer. Since the glans of the wearer generally comprises about 1.0 to 1.5 inches or so in length, in U.S. Pat. No. 5,360,390 it was stated that typically the overall length of device 1 would be about 1.0 to 1.5 inches less than the overall length of the user's partially engorged penis.

According to U.S. Pat. No. 5,360,390, from the above descriptions, a variety of alternative constructions would be readily understood. For example, it was stated that if constructed from the materials described above, the circumferential rigidity of the device 1 would have generally resulted from the material utilized to create member 3, since sheath 4 would be understood to be generally flexible material such as latex. It was also stated that member 3 could be formed from a relatively flexible material, as long as the material when in combination with sheath 4 was radially rigid. It was also stated that member 3 could be provided from somewhat flexible material formed with ribs utilized in association with stays that would provide for sufficient rigidity and relative flexibility where needed.

B. FIG. 7

It was discussed above in connection with FIGS. 1-6 that the principles described could be applied to arrangements not having a circular C-shaped configuration, but nevertheless having a generally C-shaped configuration. Such an arrangement was illustrated in FIG. 7 of U.S. Pat. No. 5,360,390, which comprised a cross-sectional view generally analogous to that of FIG. 2, for such an arrangement. Referring to FIG. 7, a device 201 in U.S. Pat. No. 5,360,390 was depicted comprising an elongate trough member 203 within sheath 204. The sheath included attached thereto mounting flap or tail 205.

According to U.S. Pat. No. 5,360,390 for the arrangement shown in FIG. 7, the trough member 203 included a central arcuate portion 210, and outer lips or flanges 211. Also according to U.S. Pat. No. 5,360,390 for the arrangement shown in FIG. 7, preferably the internal radius of curvature of portion 210 at an end corresponding to end 90 of FIG. 5 would be about 0.5 to 1.0 inches larger than the internal radius of an end corresponding to end 91. Also, in U.S. Pat. No. 5,360,390 it was stated that preferably the overall internal radius of curvature for that portion of region 210 in the vicinity of an end of the device 201 corresponding to end 91 FIG. 5 would have an internal radius of curvature of about 0.5 to about 1.5 inches. It was stated that Regions 211, on the other hand, could have a slightly tighter radius of curvature to generate the preferred configuration depicted.

C. FIGS. 8–10

Figure 9:
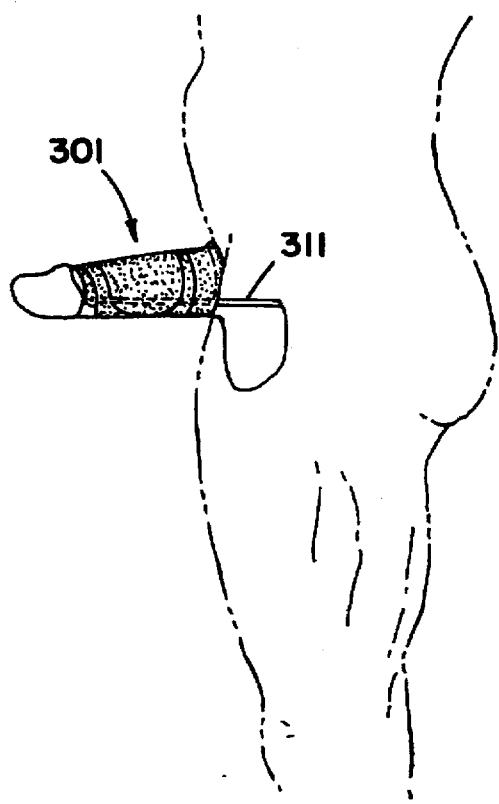
FIG. 9 is a schematic representation of the alternate prior art embodiment of FIG. 8 also depicted in U.S. Pat. No. 5,360,390 shown worn by a user.
Figure 10:
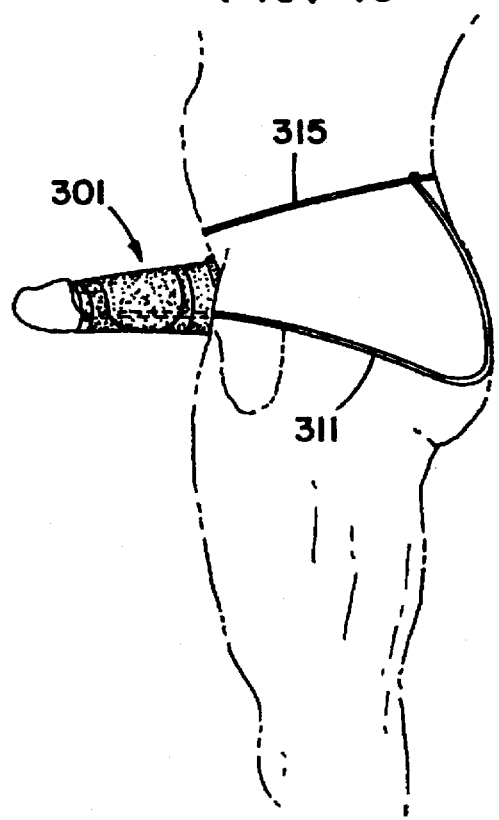
FIG. 10 is a view generally analogous to FIG. 9, of an alternate version of the prior art device of FIG. 8 shown being used by a wearer.

In U.S. Pat. No. 5,360,390 it was foreseen that in some applications it may be desirable to provide arrangements with still a further retaining means for selective positioning on a wearer. Attention is directed to FIGS. 8–10, which illustrate the disclosure of U.S. Pat. No. 5,360,390 with respect to such means.

Referring to FIG. 8, but for retaining means described herein below, a device generally analogous to that illustrated in FIG. 1 is shown in a fragmentary perspective view. That is, in FIG. 8 of U.S. Pat. No. 5,360,390, a device 301 was shown comprising an elongate generally cylindrical trough member 303 enclosed within a sheath 304 having elongate mounting flap or tail 305. Except as indicated herein below, device 301 could be generally assembled and used similarly to device 1, FIG. 1.

For the arrangement shown in FIG. 8, according to U.S. Pat. No. 5,360,390 device 301 included retaining means 310 in addition to tail 305. The retaining means 310 comprised an elongate strap 311 having first end 312 and second end 313. Strap 311 was shown fragmented at points 318 and 319. According to U.S. Pat. No. 5,360,390 in a typical application, strap 311 would be continuous in extension between points 318 and 319, the dimension, i.e. length depending upon the particular embodiment involved.

In use, stirrup or retaining strap 311 would have been mounted in association with sheath 304 by being applied to an outer (convex) surface 325 thereof. In particular, ends 312 and 313 were positioned along outer surface 325 of sheath 304. Then, when device 301 was positioned upon a wearer, tail 305 could be wrapped over both sheath 304 and ends 312 and 313 of strap 311, retaining strap 311 in association with sheath 304. If desired, strips of tape 326 or the like could be utilized to facilitate anchoring of strap 311 to sheath 304. According to U.S. Pat. No. 5,360,390 it was believed that in preferred applications strips of tape 326 would be avoided, since tail 305 would provide for some adherence. In addition, in U.S. Pat. No. 5,360,390 it was stated the strap 311 could be molded to the construction. This was described as advantageous, since the use of any adhesive in the vaginal area would preferably be avoided.

According to U.S. Pat. No. 5,360,390, preferably ends 312 and 313 of strap 311 were mounted along an exterior surface 325 of sheath 304. More specifically, it was described that they were preferably mounted on the convex side of device 301, i.e. the side opposite to wearer during use. This would facilitate comfort.

Manners in which retaining strap 311 could be utilized to facilitate operation device 301, were described in U.S. Pat. No. 5,360,390 by reference to the schematic FIGS. 9 and 10. In FIG. 9, device 301 was shown with strap 311 sized to be wrapped around the scrotum of a wearer. In FIG. 10, device 301 was shown mounted with strap 311 extending between the legs of a wearer, to the wearers backside, and upwardly into engagement with a waist loop or belt 315.

In U.S. Pat. No. 5,360,390 it was stated that from examination of FIGS. 8, 9 and 10, advantage to assist in utilizing mounting strap 311 would be understood, and, that in general, the strap 311 would help maintain device 301 in position on a wearer, without slippage.

According to U.S. Pat. No. 5,360,390 a variety of materials and sizes could be utilized for strap 311. In general, it was stated that the length would depend upon the particular wear's needs in the portion of the body about which was to be encircled.

According to U.S. Pat. No. 5,360,390 it would be preferable that strap 311 be used under relatively little tension, for comfort of the wearer; and the wearer may achieve this desired comfort level, by positioning strap 311 around the appropriate portion of the wearer's body and then laying ends 312 and 313 appropriately along device 301, before wrapping tail 305 thereover.

According to U.S. Pat. No. 5,360,390 a variety of materials could be utilized for retaining strap 311. According to U.S. Pat. No. 5,360,390 a particularly useful material would be a thin soft ribbon of rubber latex material, similar to that from which surgical tubing or the device 301 was formed. It was stated that the length would vary depending upon the particular wearer and proposed use; and also that a width dimension of about ⅛ to ⅜" would typically be sufficient, if not more than sufficient, for use and comfort. Further, it was stated that thickness would depend upon the strength of the material used.

D. FIGS. 11–15

Still another variation of the arrangements described in U.S. Pat. No. 5,360,390 is illustrated in FIGS. 11–15. The embodiment of FIGS. 11–15 comprised an improved arrangement described in that patent.

Figure 11:
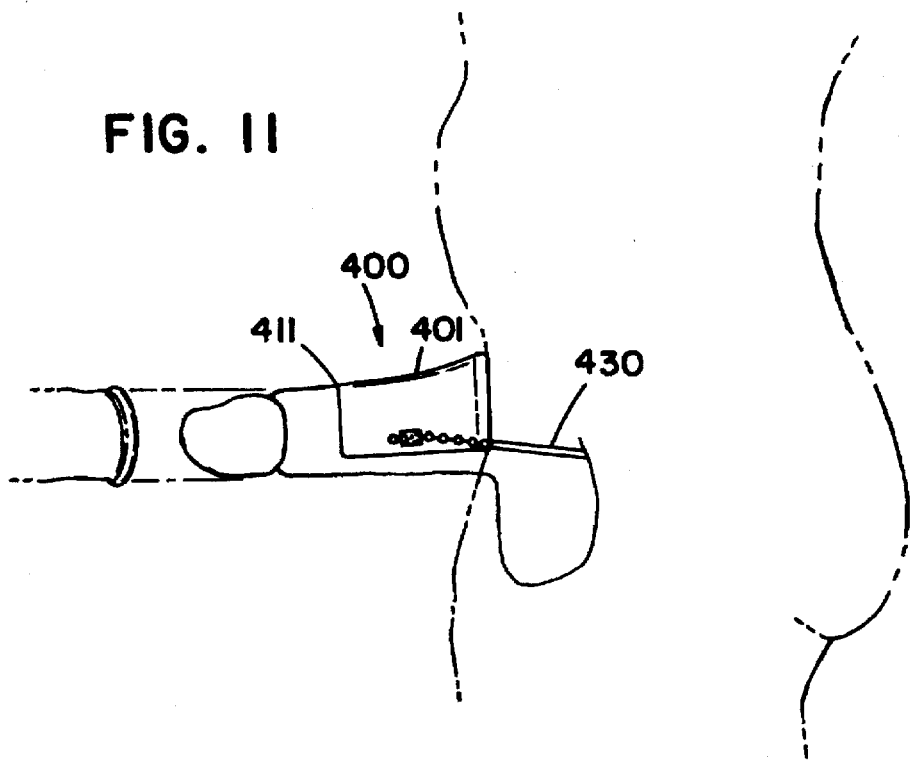
FIG. 11 is a schematic representation of a third alternate prior art device.

Referring to FIG. 11, reference numeral 400 generally designated the device. In FIG. 11 the device 400 in U.S. Pat. No. 5,360,390 was illustrated mounted at the pubic bone end of the penis and worn analogously to the device 301, FIG. 9.

Device 400 in U.S. Pat. No. 5,360,390 of FIG. 12 comprised a trough-shaped member 401 having a generally C-shaped cross-section, FIG. 13. (It will be understood that in FIG. 12 the device was illustrated in longitudinal cross-section relative to FIG. 11.)

According to U.S. Pat. No. 5,360,390 arrangement 400 shown in FIGS. 11–15 did not comprise a trough member with slots therein. Rather, according to U.S. Pat. No. 5,360,390 device 400 was a molded construction comprising flexible urethane or latex which had selected varying thicknesses throughout to achieve advantage. (It was described that injection molding may be used.) It was also described that device 400 was not provided with a sheath thereover if constructed of appropriate urethane/latex material. According to U.S. Pat. No. 5,360,390 in some instances it could be desirable to provide an outer latex coating of materials such as surgical rubber or the like.

According to U.S. Pat. No. 5,360,390 a first, major, manner in which the arrangement of FIGS. 11–15 differed from the arrangements of FIGS. 1–10 was in the nature of radial-rigidity. In general, according to U.S. Pat. No. 5,360,390 the embodiment of FIGS. 1–10 was radially rigid; i.e. it did not flex radially but rather retained its defined shape. In U.S. Pat. No. 5,360,390 it was stated that the arrangement of FIGS. 11–15 distinctly differed from this, to advantage; and, that the arrangement of FIGS. 11–15 was preferably formed from a flexible high memory material which was somewhat elastic. Thus, it could be stretched open radially, fit over the penis of a wearer and then allowed to collapse and snugly fit around the penis of a wearer. According to U.S. Pat. No. 5,360,390 a preferred, comfortable, snug fit could be obtained by shaping the article such that the position of memory or rest was at a radial size that would be comfortable for the intended user. According to U.S. Pat. No. 5,360,390 an advantage from allowing for radial flexibility was that the device could be expanded more toward one end than another; i.e. it can be expanded more toward the pubic area of the wearer than further along the shaft of the penis.

According to U.S. Pat. No. 5,360,390 preferred materials for construction of the trough member of the arrangement were FDA approved thermoplastic rubbers, such as natural (coverless) Monsanto Santoprene, in U.S.P. class no. 6. This was a pharmaceutical medical material known to be safe when positioned in a body cavity and/or when subjected to body fluids. It could be obtained from Monsanto in a variety of thicknesses, depending upon heat and pressure applied. According to U.S. Pat. No. 5,360,390 it could be readily molded into configurations such as those shown in FIGS. 11–14.

Figure 12:
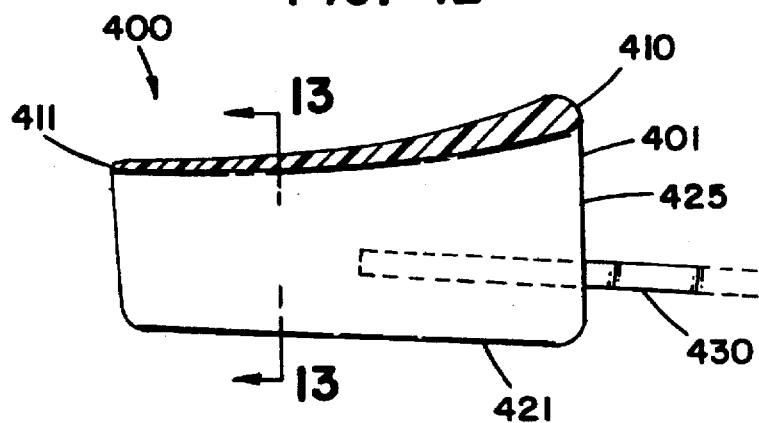
FIG. 12 is a side cross-sectional view of the prior art device of FIG. 11.

According to U.S. Pat. No. 5,360,390 another substantial difference between device 400 and the devices previously described therein concerned certain of its dimensions. In U.S. Pat. 5,360,390 it was described that, preferably, device 400 be constructed with a longitudinal dimension (length) approximately ⅓ to ⅔ (preferably at least ½) of the length of the flaccid or partially engorged penis (i.e. the penis as engorged as the particular individual was able to maintain). For the average male, the length of the partially engorged penis was described as being about 4.0 to 5.0 inches. The preferred average length of device 400, for the average male, was described in U.S. Pat. No. 5,360,390 as about 2–3 inches, and preferably about 2.25–2.75 inches. Referring to FIG. 12, the longitudinal dimension represented approximately the length of a straight line drawn between points 410 and 411.

According to U.S. Pat. No. 5,360,390 another important difference between the arrangement of FIGS. 11–15 and the arrangements previously described related to the shape and thickness of member 401. At point 411, the device 400 was relatively thin, with no bead thereon. The front 411 came to a relatively fine but rounded edge. In extension between point 411 and point 410, device 400 gradually increased in thickness up to approximately ¼–⅜ inches. The thickness increase was most pronounced along central section 415, FIG. 13. The central section 415 was the portion of device 400 centrally spaced between the two edges 420 and 421. In general use, section 415 of device 400 was positioned centrally above the penis of a wearer.

Figure 13:
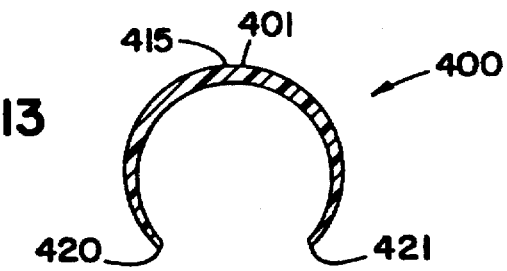
FIG. 13 is a cross-sectional view of the prior art device of FIG. 11 taken generally from the orientation of line 13—13 of FIG. 12.

In general, device 400 tapered in thickness between section 415 and each of edges 420 and 421, FIG. 13. According to U.S. Pat. No. 5,360,390 the gradual decrease in thickness facilitated comfort.

An additional advantage was described in U.S. Pat. No. 5,360,390 as resulting from the dimensions and shape described above. It was stated that the relatively thick central section 415 provided for good longitudinal strength in the root area of the penis of a wearer, facilitating support with comfort. Allowing at least approximately ⅓ (preferably at least ½) of the penis of the wearer to extend beyond the device 400, however, permitted flexibility for comfort of the wearer and the wear's sex partner. In addition, according to U.S. Pat. No. 5,360,390 under such circumstances device 400 would not penetrate very far into the female, during intercourse; and the tapering to the relatively thin edges along tip 411 and edges 420 and 421 facilitated comfort for the wearer and the wear's sex partner. Relatively thick dimension along point 410, and in general along back wall 425, FIG. 12, was described in U.S. Pat. No. 5,360,390 as facilitating positioning device 400 against the pubic area or bone of a wearer with comfort.

In U.S. Pat. No. 5,360,390 it was described that in preferred embodiments, the inner surface of device 400 was provided with pebbling, to increase its coefficient of friction against skin, to help retain the device 400 in place, during use.

Unlike with certain arrangements in FIGS. 1–10, according to U.S. Pat. No. 5,360,390 the arrangement of FIGS. 11–15 did not involve mounting with a wrap-around tongue or sheath. Rather, the arrangement of FIGS. 11–15 was mounted with a stirrup or strap 430. The strap 430 was connected at opposite ends to the trough member 401. The strap 430 was sized to extend around a portion of the body of a wearer. According to U.S. Pat. No. 5,360,390 it could extend, for example, around the scrotum of a wearer similarly to the strap illustrated in FIG. 9. In the alternative, it was described that it could be mounted similarly to the strap illustrated in FIG. 10.

Figure 14:
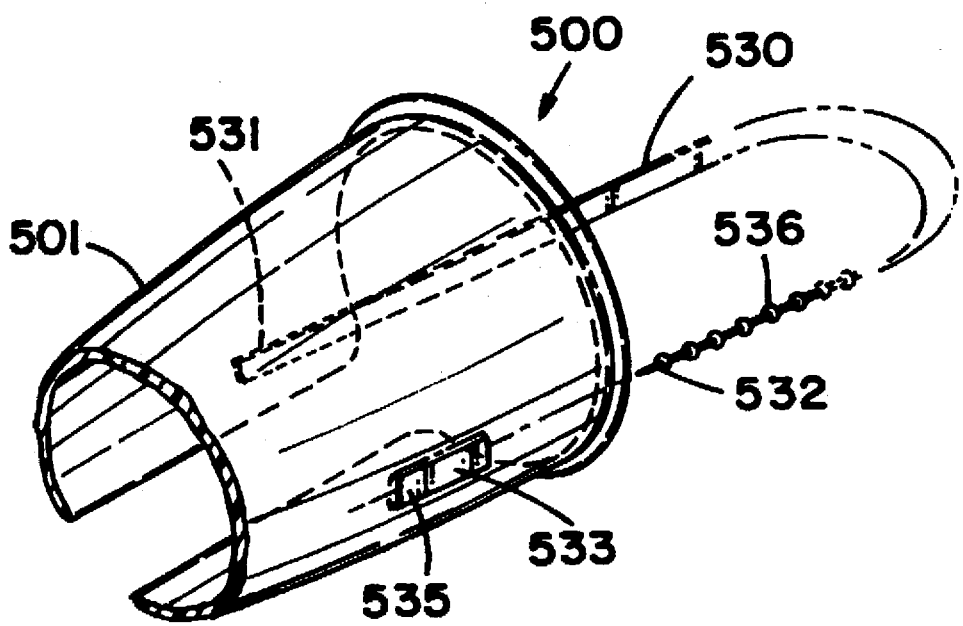
FIG. 14 is a fragmentary perspective view of the prior art arrangement shown in FIGS. 11–13, with a first means of mounting an engagement strap depicted.
Figure 15:
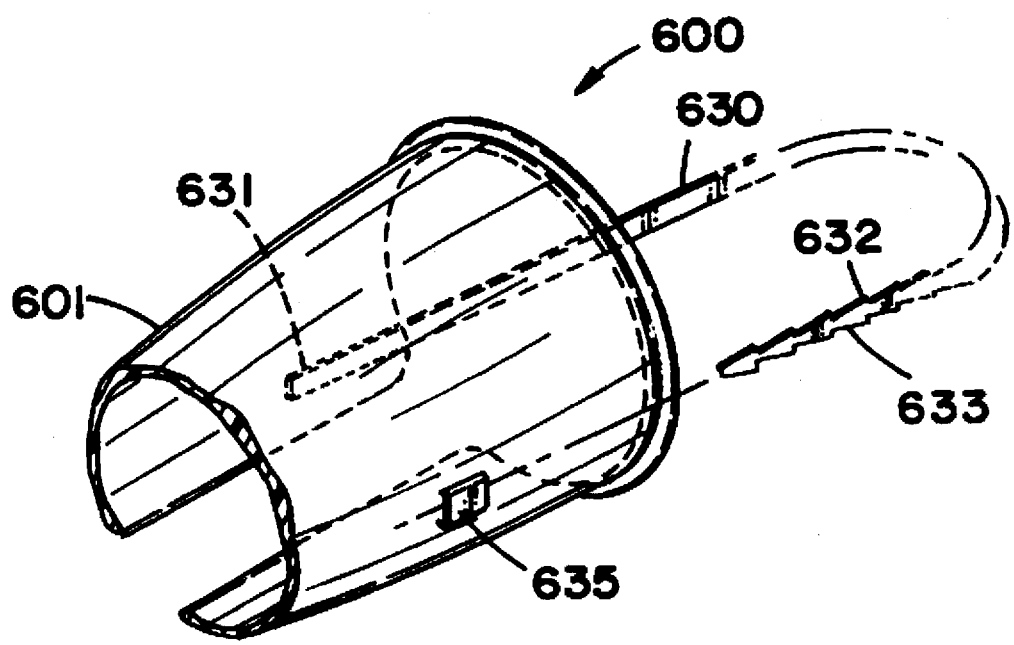
FIG. 15 is a fragmentary perspective view generally analogous to FIG. 14, with an alternate means of mounting an engagement strap illustrated.

Attention is directed to FIGS. 14 and 15 with respect to alternate methods of mounting the strap 430. According to U.S. Pat. No. 5,360,390 in the arrangement 500 illustrated in FIG. 14, the strap 530 was connected at one end 531 by molding or similar means; and, the opposite end 532 of the strap 530 included means thereon for engagement with connector means 533 on the trough member 501. In the arrangement of FIG. 14, connection was facilitated by a low-profile slot arrangement 535 engageable by a ball and link type fastener 536. According to U.S. Pat. No. 5,360,390 the user would extend end 536 into the slot of connector 535, adjusting the amount of extension into the slot for comfort; and the excess portion of end 532 would be torn or cut off and discarded. When the device 500 was to be removed, a remaining link could be premolded to break, preventing reuse.

According to U.S. Pat. No. 5,360,390 the arrangement 600 in FIG. 15 illustrated an alternate mounting system for strap 630. Strap 630 was connected at end 631 to trough member 601. According to U.S. Pat. No. 5,360,390 the connection could be made by molding or similar means. At end 632 strap 630 included "ratchet" or "directional tooth" fastener 633, receivable within connector 635. According to U.S. Pat. No. 5,360,390 the user could adjust the length of strap 630 by the extent to which end 632 was threaded through a receiving slot in connector 635; and, the excess portion of the connector on end 632 could be torn or cut off and discarded. The portion of strap 630 having tooth fastener 633 thereon could be readily torn, for removal of the device 600 from a user.

It was described in U.S. Pat. No. 5,360,390 that the arrangements of FIGS. 14 and 15 were exemplary only, and a variety of attachment means could be utilized. For example, it was described that for the arrangements shown in FIGS. 11–15, both ends of the straps were shown mounted on the exterior surface of trough member 401, and that alternate attachments (involving an interior surface) could be utilized in some instances. Also, the straps could have connection means at both ends.

As with previously described arrangements, for the arrangement of FIGS. 11–15 the "gap" in the C cross-section (distance between edges 420 and 421) when the device was worn was described in U.S. Pat. No. 5,360,390 as being at least about 0.5 inches, and for the average male about 0.75–1.5 inches. For embodiments having a circular cross-section, a radial gap of 50° to 110° was generally preferred. According to U.S. Pat. No. 5,360,390 these dimensions would not necessarily be maintained by the device when it was not worn, since it was radially flexible and could curl to a smaller diameter or radial dimension. According to U.S. Pat. No. 5,360,390 if the device was of an appropriately soft, memory material, it could be easily expanded and snugly fit on a user.

It was described in U.S. Pat. No. 5,360,390 that preferred arrangements according to FIGS. 11–15 would be manufactured as "single use" devices. That is, they would be used once and discarded. According to U.S. Pat. No. 5,360,390 it was an advantage of the embodiment depicted in FIGS. 11–15 that it could be inexpensively manufactured, thus facilitating single use.

II. Detailed Description of Arrangements According to the Present Invention:

A. FIGS. 16–23

As indicated above, FIGS. 1–15 reflect the arrangements described in U.S. Pat. No. 5,360,390 issued Nov. 1, 1994, and assigned to Gain, Inc. The description provided above with respect to these arrangements, reflects the substance of descriptions provided in that patent.

Since the time of issuance of U.S. Pat. No. 5,360,390, Gain, Inc., the assignee of the present invention, has developed improvements in the arrangement (prosthesis) while preparing the arrangement for marketing. The improvements in connection with the arrangement are presented herein and are reflected in the drawings of FIGS. 16–23. It will be understood that the arrangement of FIGS. 16–23 in many ways functions generally analogously to the arrangements described in connection with FIGS. 1–15, and may be, except as described hereinbelow, constructed from similar materials and of similar dimensions. Certain specific improvements are provided, however, to advantage.

Figure 16:
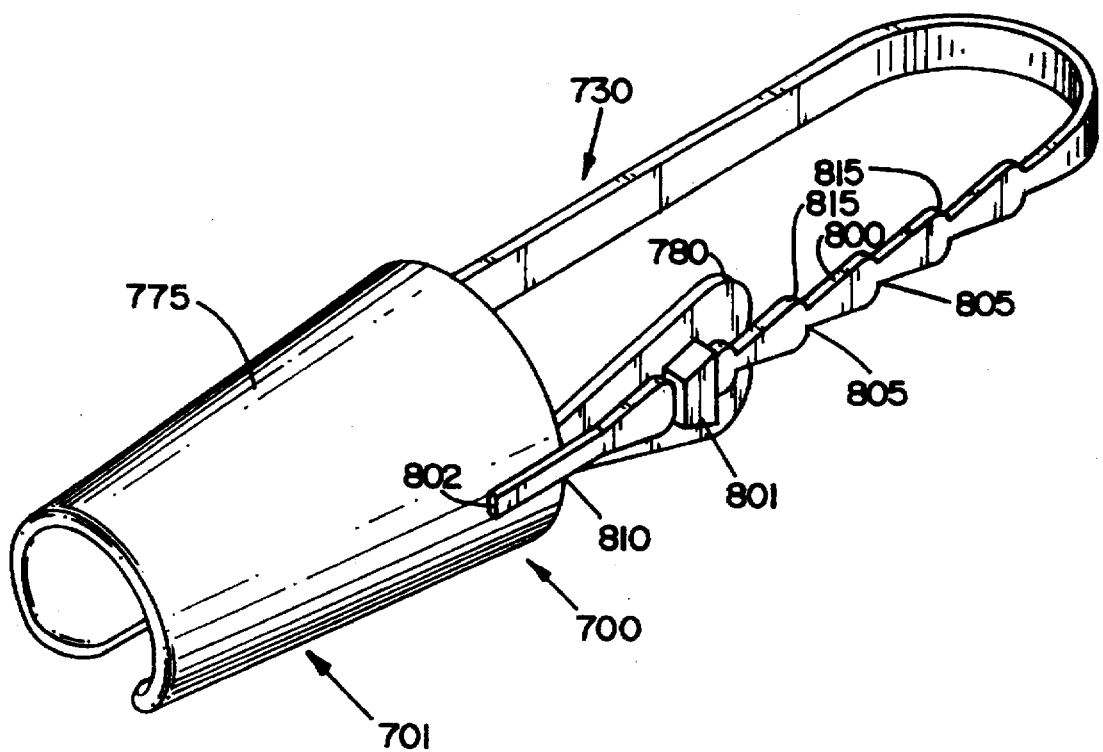
FIG. 16 is a perspective view of an improved device according to the present invention.
Figure 17:
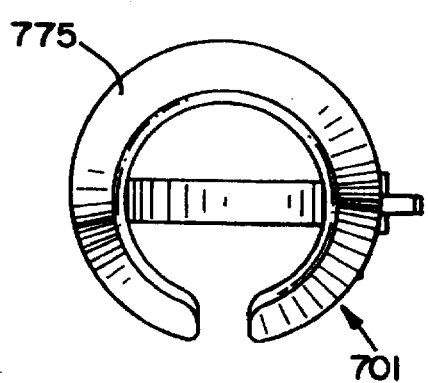
FIG. 17 is an end elevational view of the arrangement shown in FIG. 16.

Referring first to FIG. 16, the prosthesis or arrangement is shown generally at reference numeral 700. Preferably, the entire arrangement 700 is a molded construction comprising flexible urethane or latex, most preferably the preferred Monsanto Santoprene described above. That is, most preferably the arrangement 700 is of unitary construction, completely molded, with no attached parts that are not part of the integrally molded construction; i.e. there are no seams or points of similar attachment.

The arrangement 700 generally includes one elongate trough or trough-shaped member 701; and, a mounting strap 730. The trough member is sized to fit over a penis of a user at a location immediately in front of the pubic bone. The trough member preferably has a C-shaped cross section and longitudinal slot extending completely thereacross, as described and shown the slot is on an underside of the trough 701, similarly to arrangements previously described.

Figure 23:
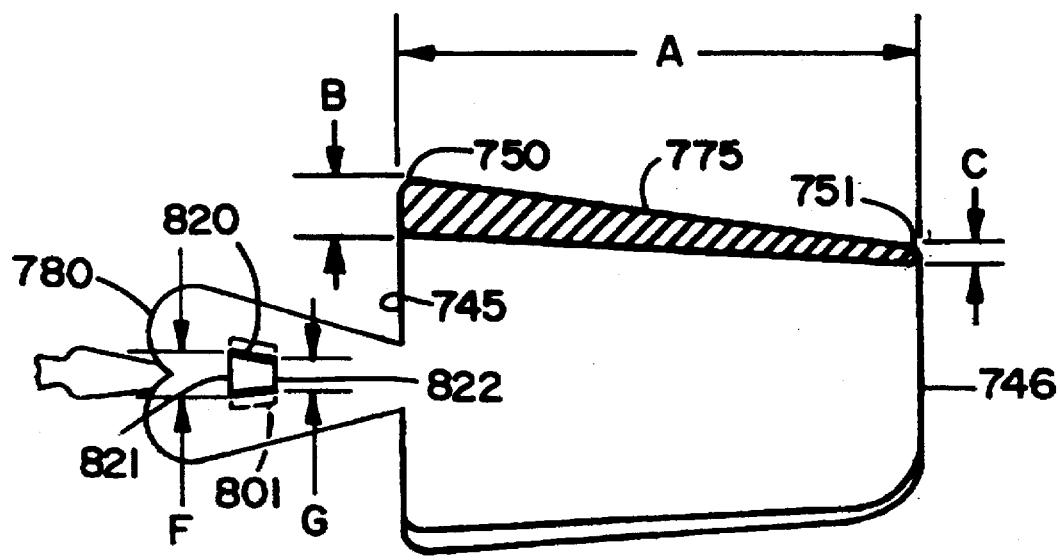
FIG. 23 is a fragmentary cross-sectional view taken generally along line 23—23, FIG. 21.

In addition to being molded from the Monsanto Santoprene described above, preferably the trough member 701 of arrangement 700 is as follows: its overall length, preferably as measured in projection as indicated in FIG. 23 at dimension A, is preferably 2–4 inches, more preferably 2.25–2.75 inches, and for the preferred construction is about 2.44 inches. (By "in projection" reference is meant to the length of the projected image, as shown, which may be slightly shorter than the actual length of the surface.) The thickness at dimension B, FIG. 23, is preferably about 0.2–0.3 inches, most preferably about 0.22–0.28 inches, and in the preferred commercial arrangement is about 0.25 inches. The overall analogous thickness at the end represented at C, in FIG. 23, is preferably about 0.02–0.08 inches, most preferably about 0.05 inches. In the preferred arrangements, the trough member is molded from a material that has a durometer reading of less than 70, more preferably a durometer reading of 55 to 65, and most preferably a durometer reading of 64. Preferably, the inside dimension at end 745, FIG. 23, is molded to a radius of curvature of about 0.55–0.9 inches, preferably about 0.62–0.75 inches, most preferably about 0.69 inches. Of course, because the material is preferably a flexible Santoprene, once removed from the mold it may curl to a smaller radius of curvature, but it will readily flex to the appropriate radius of curvature if of the thickness as described. Preferably, the analogous inside radius of curvature at end 746, FIG. 23, is molded to a radius of curvature of about 0.05–0.2 inches smaller than the inside radius of curvature of end 745, and in typical preferred arrangements it is a radius of curvature of about 0.5–0.63 inches and preferably about 0.55–0.58 inches. Most preferably it is about 0.56 inches when end 745 is about 0.69 inches. In use, the arc made by the preferred embodiment of the trough-shaped member 701 will consist of an arc of between about 200 to 340 degrees, and most preferably between about 240 to 300 degrees.

The radii of curvature at certain portions of the arrangement have been designed for preferred levels of comfort. The radius of curvature at edge 750 (the outer edge of end 745) is preferably molded to a radius of about 0.03–0.1 inches, more preferably at least about 0.05 inches, and for the preferred arrangement about 0.06 inches. The radius of curvature at edge 751 (the outer edge of end 746) is preferably 0.01–0.04 inches, most preferably about 0.02–0.03 inches, and for the most preferred arrangement is about 0.025 inches.

Figure 22:
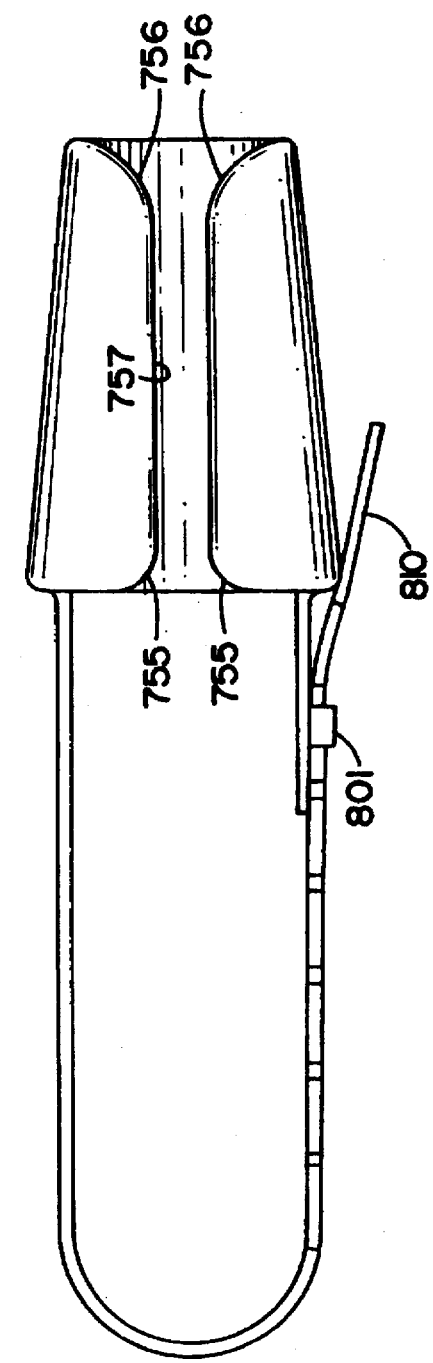
FIG. 22 is a bottom plan view of the arrangement shown in FIG. 16.

Referring to FIG. 22, preferably the radius of curvature for edges or corners 755 is about 0.1–0.3 inches, most preferably about 0.2–0.25 inches, and for the preferred arrangement is 0.22 inches. Slot 757, FIG. 22 may be as described above for FIGS. 11–15, with a similar width and definition by arcuate extension.

At corners 756, FIG. 22, preferably the radius of curvature is about 0.02–0.08 inches, more preferably 0.03–0.07, and for the most preferred arrangement is about 0.05 inches.

It has been found that when molded to the general dimensions described hereinabove, arrangements 700 according to the present invention will be shaped in a convenient, comfortable, manner that is effective for facilitating use, on the average wearer.

Attention is now directed to features which concern the mounting strap 730, FIG. 16, and the manner in which it is mounted in the arrangement 700. The mounting strap serves as part of a form of retaining structure for maintaining the trough member in operative association over the user's penis, during intercourse. Although alternatives are possible, the preferred retaining structure comprises a retaining strap 730 and an associated tab 780.

Figure 21:
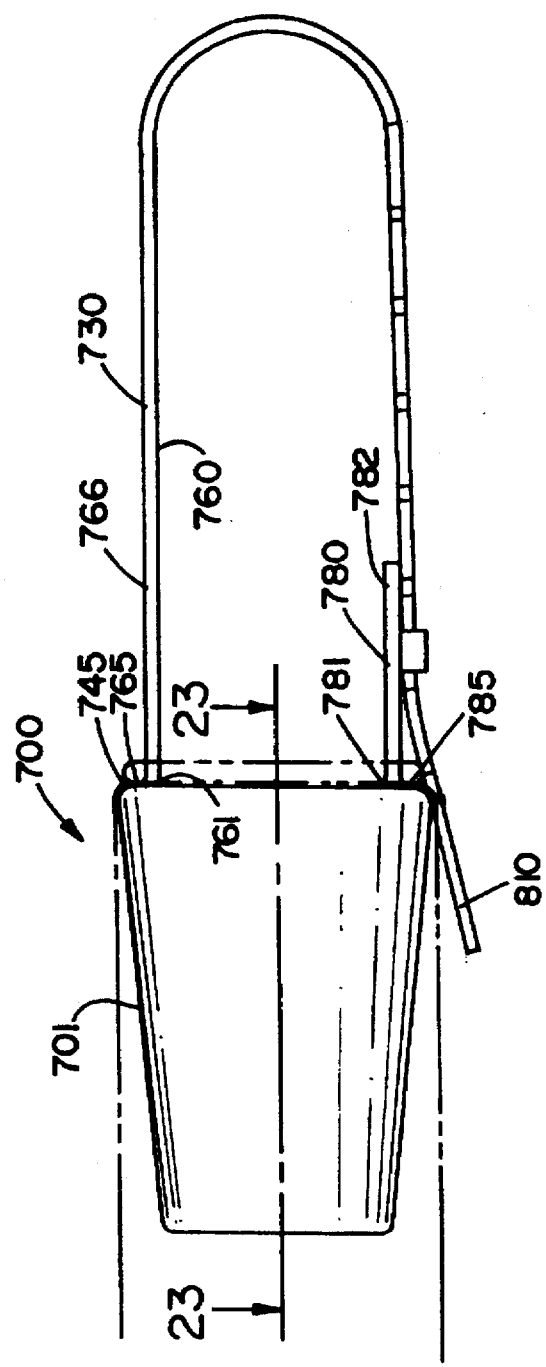
FIG. 21 is a top plan view of the arrangement shown in FIG. 16.

Referring to FIG. 21, strap 730 is part of the overall molded arrangement 700 and, thus, is integral with portion 701, i.e. there is no seam therebetween. Preferably, it is molded such that an inside surface 760 of strap 730 is essentially flush with (or coplanar with) an inside surface of portion 701. By constructing the overall molded arrangement 700 such that an inside surface 760 of strap 730 is essentially flush with (or coplanar with) an inside surface of portion 701, instead of having the inside surface 760 or an outside surface 766 of strap 730 essentially flush with (or coplanar with) end 745 of trough member 701, the strap 730 is much less likely to break away from the end 745 of trough member 701, in use. Also preferably strap 730, at point 761, FIG. 21, whereat it is attached to trough member 701, has a thickness which is no more than about two-thirds of the thickness of end 745 of trough member 701 at this location. Preferably, the thickness of strap 730 is about 0.02–0.1 inches, more preferably about 0.05–0.09 inches, and for the most preferred arrangement described is about 0.07 inches, throughout. In the preferred embodiments, preferably an outer lip or shoulder at 765 where strap 730 attaches to trough member 701 is left. This lip or shoulder 765 provides a recess into which an open end of a condom or lubricated cover, shown in phantom in FIG. 21 at reference numeral 770, can be positioned (rolled) in use. This shoulder 765 will tend to retain the condom or lubricated cover securely on the user and arrangement 700, during use, to advantage. In some preferred embodiments this is facilitated by the absence of a bead along outer surface 775, of trough member 701, FIG. 16. That is, referring to the cross-section of FIG. 23, in some preferred embodiments outer surface 775 generally is flat or planar, with the curved ends as described, and it does not have an upwardly or outwardly raised bead or projection thereon, at any location, and the outer surface 775 has rounded ends 751 and 750 as described. In other preferred embodiments, outer surface 775 may have a series of raised ribs along its length, or a series of bumps or other surface configurations.

Referring to FIG. 21, preferably the arrangement 700 includes a receiving tab 780 molded to trough shaped member 701 at a location 781 generally opposite of location 761 whereat strap 730 attaches. Preferably, member 780 has a thickness generally the same as that of the strap 730. Also preferably, it is analogously molded with an inside surface 782 essentially flush or coplanar with an inside surface of trough shaped member 701. Further, preferably it is molded such that shoulder 785, analogous to shoulder 765, is provided, for analogous reasons.

Figure 20:
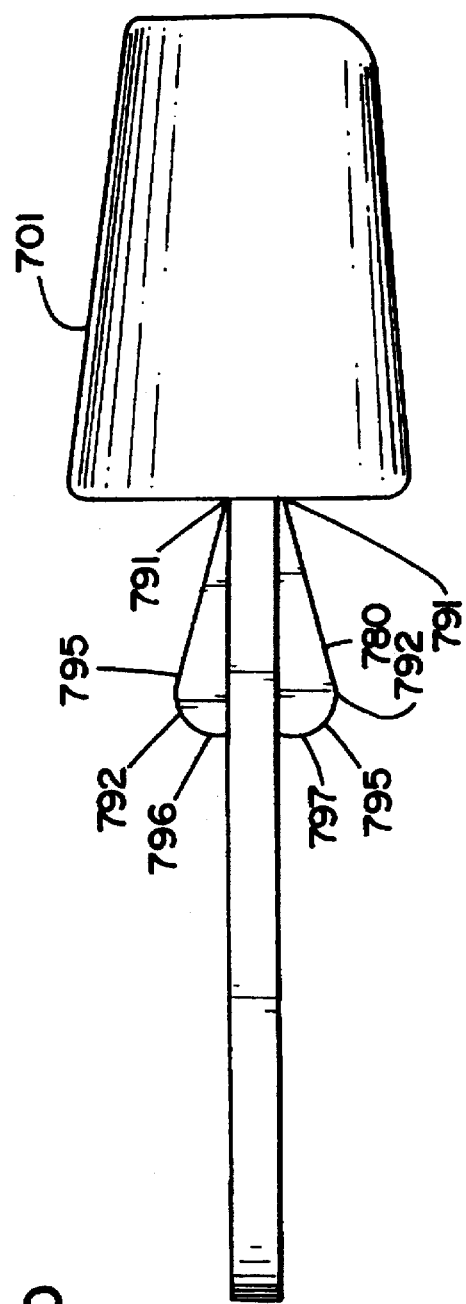
FIG. 20 is an opposite side elevational view to that shown in FIG. 19.

Referring to FIG. 20, preferably member 780 has a relatively narrow dimension at location 791 whereat it is attached to trough shaped member 701, and a relatively wider dimension, somewhere else throughout its extension. For the arrangement shown in FIG. 20, the relatively wide dimension occurs between points 792. This facilitates operation. First, the relatively narrow dimension at region 791 helps provide for such features as: ease of molding and secure positioning of a condom or lubricated cover over the arrangement. The relatively wide dimension between points 792, however, facilitates comfort of wearer, since it expands the width of tab 780 where it rests against the skin of user. In preferred arrangements, between points 791, FIG. 20, the arrangement 700 has a dimension of about 0.75 to 1 inches and preferably about 0.87 to 0.94 inches. Also for preferred arrangements, the tab or member 780 has a dimension thereacross, at its widest point, of at least 1.1 times that of the dimension between points 791; with the dimension being typically about 0.12 to 0.88 inches and most preferably at least about 0.37 inches.

Figure 19:
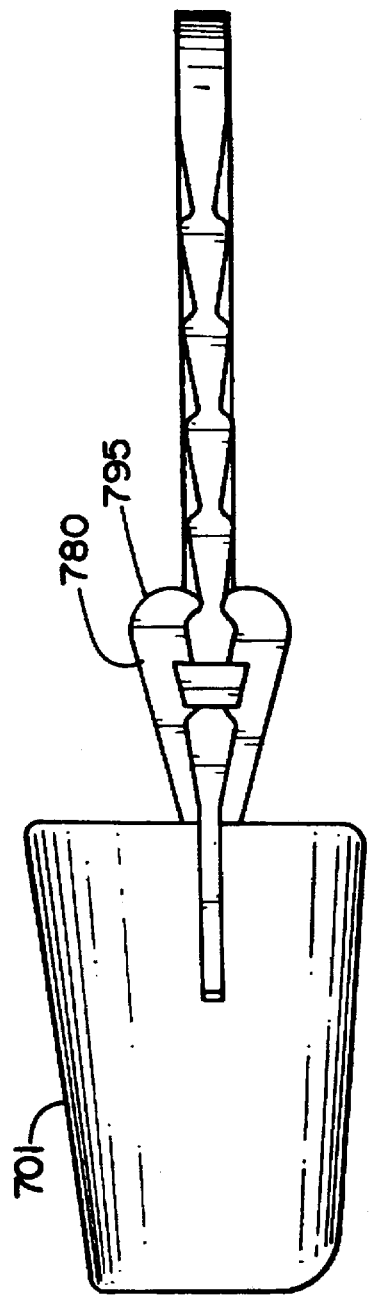
FIG. 19 is a side elevational view of the arrangement shown in FIG. 16.

The particular "heart shaped" outer configuration for member 780 illustrated in FIGS. 19 and 20, by periphery 795, provides no distinct advantage, and is present as an artistic feature for aesthetic purposes. Also, in part, it was designed to also serve a distinctive source identifying function, i.e. that the arrangement originated with the present assignee. It will be readily understood that advantageous narrow portions at area 791, and a wide portion somewhere else in member 780 could be accomplished with many variations in outer periphery. The two rounded lobes at 796 and 797, provide a somewhat "heart-shaped" design, and do not specifically serve advantage.

Again, there is, however, advantage to having a relatively wide portion as indicated between points 792. A wide dimension at such a location, in tab 780, provides for comfort for the wearer, and avoids a relatively narrow strap which might tend to dig into the skin of the wearer a bit more at this location. The relatively wide portion as indicated between points 792 also has advantage by reducing the pulling of the user's pubic hairs when strap 730 is being attached to tab 780.

Referring to FIG. 16, strap 730 includes a notched section 800 therein, and tab 780 includes a locking arrangement such as a catch 801 therein, for receiving end 802 of strap 730 therethrough. In preferred arrangements the length of strap 730 from point 761 to the beginning of the notched section 800 is about 3–6 inches in length, and most preferably is about 4.5 inches in length. A variety of designs can be utilized for notches 805 and catch 801. For the arrangements shown, catch 801 is a raised slot through which selected notches 805 extend. In preferred embodiments, the raised slot has a height of about 0.03–0.11 inches, more preferably about 0.06–0.10 inches, and for the most preferred arrangement described is about 0.08 inches. All that is generally required is a secure arrangement, to facilitate attachment of the wearer. For typical preferred arrangements, strap 730 from end to end will be molded to be about 9 to 11 inches long, so that it can be used conveniently by a variety of users, and tab 780 will be about 1 to 1.5 inches long, most preferably about 1.19 inches long. If desired, the user could cut off the extension or tab 810 projecting beyond catch 801, FIGS. 16 and 22, after the device 700 has been positioned on the user, for comfort. It could be retained, however, in many instances. In connection with this, referring to FIG. 21, the tab 810 is shown projecting on the outside of the condom or lubricated cover. It could alternatively be positioned under the condom or lubricated cover, if desired. As a further alternative, tab 810 could be cut to a length that would allow it to rest substantially parallel to tab 780, between a catch arrangement 801, FIG. 16, with the distal end of tab 810 being truncated so as not to extend as far as the condom or lubricated cover.

Devices as shown in FIGS. 16 through 23 could be manufactured for single use, or for multiple use. When multiple use is desired, it will be preferred to have a catch arrangement 801, FIG. 16, which, although secure, does allow for retraction of tab 810 for disconnection. Rounded edges 815, on notches 805, FIG. 16, facilitate this. In the preferred embodiments, the rounded edges 815 are about 0.12–0.4 inches in width, and most preferably about 0.25 inches in width. In preferred embodiments, the notches 805 and tab 810 are 0.07–0.20 inches in width, and most preferably about 0.12–0.13 inches in width. To facilitate insertion and removal of tab 810 with catch arrangement 801, it is preferable to have the rounded edges 815 have a radius of curvature in the range of 0.03–0.09 inches, most preferably 0.06 inches. In the preferred embodiments, it is preferable to have the notches 805 also somewhat rounded, preferably in a range of 0.005–0.02 inches, most preferably 0.01 inches. In order to accommodate a variety of individual sizes, it is preferable to have a plurality of pairs of rounded edges 15 provided on Section 800 of strap 730, more preferably, a series of 4–14 such pairs of rounded edges 815 are provided, and most preferably eight pairs of rounded edges 815 are provided. The distance between a first pair of rounded edges 815 and a second adjacent pair of rounded edges 815 is preferably in the range of about 0.25–1 inches, and most preferably about 0.5 inches. The length of tab 810 is preferably in the range of about 0.5–2 inches, and most preferably about 1 inch.

Referring to FIG. 23, catch 801 has an opening 820 to receive strap 730, such that the strap 730 may be lockingly retained by any of the pairs of rounded edges 815 on Section 800 of strap 730. In order to facilitate insertion of end 802 of tab 810 into opening 820 of catch 801, it is more preferable that opening 801 have a first end 821 with a width F that is wider than the width of tab 810. Also in the preferred embodiments, it is advantageous to have the opening 820 have a second end 822 with a width G that is smaller than width F of end 821, but larger than tab 810, more preferably, width G is in the range of about 0.01–0.25 inches in width, and most preferably 0.15 inches in width.

Referring to FIG. 23, in preferred arrangements the distance between ends 821 and 822 of opening 820 is about 0.1–0.3 inches, and most preferably about 0.19 inches. In the preferred arrangements, end 822 of opening 821 is located in the range of 0.05 to 0.75 inches from end 745 of trough member 700, most preferably in the range of about 0.06 to 0.4 inches. Also in the preferred embodiments, tab 780 has a length of 1 to 2 inches, most preferably a length of 1.25 to 1.5 inches.

For preferred arrangements, strap 730 is about 0.28 to 0.35 inches wide. Such a width will be comfortable for the wearer and convenient to use.

Figure 18:
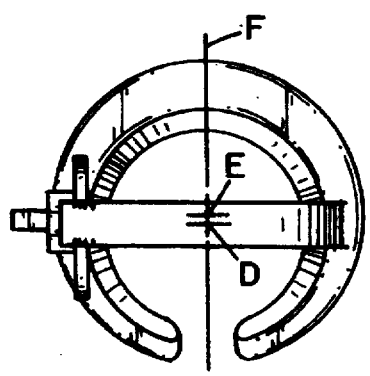
FIG. 18 is an opposite end elevational view to that shown in FIG. 17.

The outside diameter at end 745, FIG. 23, is molded to a diameter of 1.3–2.4 inches, preferably about 1.5–2 inches, most preferably about 1.75 inches. In the most preferred embodiment the inside diameter at end 745, FIG. 23 is concentric with the inside diameter at end 746, FIG. 23, as illustrated in FIG. 18 at D. However, in that most preferred embodiment, the outside diameter at end 745, FIG. 23 is offset from the inside diameter at end 745, FIG. 23 in the direction along line F, FIG. 18 toward point E, FIG. 18 a distance of about 0.15 to 0.25 inches, typically about 0.2 inches.

What is claimed and desired to be secured by letters patent is as follows:

1. A prosthesis for use by a human male in supporting the penis during intercourse; said prosthesis comprising:
   (a) an elongate trough member sized to fit over a penis of a user at a location immediately in front of the pubic bone;
      (i) said trough member having a C-shaped cross-section with longitudinal slot extending completely thereacross, on an underside thereof;
      (ii) said trough member having an outer surface with first and second ends;
   (b) a retaining construction for maintaining the trough member in operative association over the user's penis, during performance of intercourse; said retaining construction comprising: a retaining strap having first and second ends; and, a retaining tab;
      (i) said retaining strap and retaining tab each being secured to said trough member second end;
      (ii) said retaining strap being constructed and arranged for selective locking engagement with said retaining tab, in use;
   (c) each of said retaining strap and said retaining tab being thinner than said second end of said trough member;
      (i) said retaining strap and retaining tab each being secured to said trough member with a shoulder formed along said trough member second end, between each of said retaining strap and retaining tab, and an outer surface of said trough member; and,
   (d) said prosthesis comprising a unitary, molded, construction without any attachment seams.

2. A prosthesis according to claim 1 wherein:
   (a) said retaining tab has a first end whereat it is molded to said trough member; said first end of said retaining tab having a first dimension of width; and,
   (b) said retaining tab is configured to have a second dimension of width, at a portion thereof spaced from said trough member, said second dimension of width being greater than said first dimension of width.

3. A prosthesis according to claim 2 wherein:
   (a) said second dimension of width is 1 to 4 times larger than said first dimension of width.

4. A prosthesis according to claim 2 wherein:
   (a) said second dimension of width is at least 0.75 times larger than said first dimension of width.

5. A prosthesis according to claim 2 wherein:
   (a) said first dimension of width is within the range of 0.25 to 0.5 inches; and,
   (b) said second dimension of width is within the range of 0.5 to 1 inches.

6. A prosthesis according to claim 1 wherein:
   (a) said trough member has an overall length, in projection, of 2 to 4 inches.

7. A prosthesis according to claim 1 wherein:
   (a) said trough member first end has an inside edge having a radius of curvature that is less than 0.03 inches.

8. A prosthesis according to claim 1 wherein:
   (a) said trough member first end has an outside edge having a radius of curvature between 0.02 to 0.03 inches.

9. A prosthesis according to claim 1 wherein:
   (a) said trough member second end has an inside edge having a radius of curvature that is less than 0.03 inches.

10. A prosthesis according to claim 1 wherein:
    (a) said trough member second end has an outside edge having a radius of curvature between 0.05 to 0.10 inches.

11. A prosthesis according to claim 1 wherein:
    (a) said trough member first end has a thickness of between 0.02 to 0.08 inches.

12. A prosthesis according to claim 1 wherein:
    (a) said trough member second end has a thickness of between 0.22 to 0.28 inches.

13. A prosthesis according to claim 1 wherein:
    (a) said trough member first end is rounded and has a radius of curvature of between 0.55 to 0.58 inches.

14. A prosthesis according to claim 1 wherein:
    (a) said trough member second end is rounded and has a radius of curvature of between 0.62 to 0.75 inches.

15. A prosthesis according to claim 1 wherein:
    (a) said trough member is a molded construction comprising flexible urethane.

16. A prosthesis according to claim 1 wherein:
    (a) said trough member is a molded construction comprising latex.

17. A prosthesis according to claim 1 wherein:

(a) said trough member is planar, in longitudinal cross-section in extension between said first and second ends, with no raised ribs thereon.

18. A method of preparing a human male for sexual activity; said method comprising the steps of:

(a) fitting over a user's penis a prosthesis comprising:
  (i) an elongate trough member sized to fit over a penis of a user at a location immediately in front of the pubic bone; said trough member having a C-shaped cross-section with longitudinal slot extending completely thereacross, on an underside thereof; said trough member having an outer surface with first and second rounded ends; said trough member being planar, in longitudinal cross-section in extension between said first and second ends, with no raised ribs thereon;
  (ii) retaining means for maintaining the trough member in operative association over the user's penis, during performance of intercourse; said retaining means comprising: a retaining strap having first and second ends; and, a retaining tab; said retaining strap and retaining tab each being secured to said trough member's second end; said retaining strap having structure thereon for selective locking engagement with said retaining tab, in use;
  (iii) each of said retaining strap and said retaining tab being thinner than said second end of said trough member; said retaining strap and retaining tab each being secured to said trough member with a shoulder formed along said trough member second end, between each of said retaining strap and retaining tab, and an outer surface of said trough member; and,
  (iv) said prosthesis comprising a unitary, molded, construction without any attachment seams;

(b) said step of fitting the user's penis with the prosthetic device including:
  (i) positioning the prosthesis over the penis on a side thereof toward the user's belly and with the longitudinal slot in the C-shaped cross-section directed away from the user's belly;
  (ii) positioning the retaining strap around the user's scrotum;
  (iii) engaging the retraining strap with the retaining tab; and,
  (iv) positioning the second end of the prosthesis proximate the pubic area of the male user.

19. A method of preparing a human male for sexual activity according to claim 18 wherein:

(a) said step of fitting the user's penis with the prosthetic device further includes positioning a lubricated cover over the penis and prosthesis.

20. A method of preparing a human male for sexual activity according to claim 18 wherein:

(a) said step of fitting the user's penis with the prosthetic device further includes positioning a condom over the penis and prosthesis.

* * * * *